United States Patent
Blay et al.

(10) Patent No.: US 6,225,498 B1
(45) Date of Patent: May 1, 2001

(54) METHOD OF REMOVING ORGANIC IODIDES FROM ORGANIC MEDIA

(75) Inventors: George A. Blay; Jerry A. Broussard; G. Paull Torrence, all of Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/534,868

(22) Filed: Mar. 24, 2000

(51) Int. Cl.[7] .................................................. C07C 51/42
(52) U.S. Cl. .............................................................. 562/608
(58) Field of Search ................................. 562/608, 898; 554/191; 210/690

(56) References Cited

U.S. PATENT DOCUMENTS

| | | | |
|---|---|---|---|
| 4,615,806 | 10/1986 | Hilton | 210/690 |
| 5,139,981 | 8/1992 | Kurland | 502/11 |
| 5,220,058 | 6/1993 | Fish et al. | 562/608 |
| 5,227,524 | * 7/1993 | Jones | 562/608 |
| 5,416,237 | 5/1995 | Aubigne et al. | 562/519 |
| 5,801,279 | 9/1998 | Miura et al. | 562/608 |

FOREIGN PATENT DOCUMENTS

| | | | |
|---|---|---|---|
| 0 482 787 A2 | 4/1992 | (EP) | C07C/51/47 |
| 0 685445 B1 | 5/1995 | (EP) . | |

* cited by examiner

*Primary Examiner*—Gary Geist
*Assistant Examiner*—John N. Calve
(74) *Attorney, Agent, or Firm*—James J. Mullen; Michael W. Ferrell

(57) ABSTRACT

A method of removing organic iodides from non-aqueous organic media includes contacting the organic media with a silver or mercury-exchanged cationic ion exchange substrate at a temperature greater than about 50° C. The method is particularly effective for removing high molecular weight organic iodides from organic media such as acetic acid or acetic anhydride. Particular species removed include decyl iodides and dodecyl iodides from organic media such as acetic acid.

29 Claims, 3 Drawing Sheets

EX. A FEED = 540 ppb
EX. B FEED = 238 ppb

DODECYL IODIDE REMOVAL VS. TEMPERATURE

REMOVAL OF NEOPENTYL IODIDE AT 25°C
COMPARISON WITH HEXYL IODIDE

ELUTION ISOTHERMS FOR DODECYL IODIDE

METHOD OF REMOVING ORGANIC IODIDES FROM ORGANIC MEDIA

TECHNICAL FIELD

The present invention relates generally to the removal of iodides from organic media and more particularly to the removal of higher iodides, such as dodecyl iodide from acetic acid and/or acetic anhydride manufactured by utilizing a rhodium-Iodide catalyst system.

BACKGROUND ART

Perhaps the most widely used process for the manufacture of acetic acid, the well known Monsanto process, involves carbonylating methanol in the presence of rhodium, methyl iodide, methyl acetate and water. The product is suitable for all purposes; however, iodide contamination is an issue with respect to acetic acid made by way of the Monsanto process or in acetic anhydride manufactured by way of a rhodium-iodide catalyst system.

It was discovered by Hilton that macroreticulated, strong acid cationic exchange resins with at least one percent of their active sites converted to the silver or mercury form exhibited remarkable removal efficiency for iodide contaminants in acetic acid or other organic media. The amount of silver or mercury associated with the resin may be from as low as about one percent to as high as 100 percent. Preferably about 25 percent to about 75 percent of the active sites were converted to the silver or mercury form and most preferably about 50 percent. There is disclosed in U.S. Pat. no. 4,615,806 removal of various iodides from acetic acid. In particular there is shown in the examples removal of methyl iodide, HI, $I_2$ and hexyl iodide.

Various embodiments of the basic invention disclosed in U. S. Pat. No. 4,615,806 have subsequently appeared in the literature. There is shown in U.S. Pat. No. 5,139,981 to Kurland a method for removing iodides from liquid carboxylic acid contaminated with a halide impurity by contacting the liquid halide contaminant acid with a silver (I) exchanged macroreticular resin. The halide reacts with the resin bound silver and is removed from the carboxylic acid stream. The invention in the '981 patent more particularly relates to an improved method for producing the silver exchanged macroreticular resins suitable for use in iodide removal from acetic acid.

U.S. Pat. no. 5,227,524 to Jones discloses a process for removing iodides using a particular silver-exchanged macroreticular strong acid ion exchange resin. The resin has from about 4 to about 12 percent cross-linking, a surface area in the proton exchanged form of less than 10 m2/g after drying from the water wet state and a surface area of greater than 10 $m^2$/g after drying from a wet state in which the water has been replaced by methanol. The resin has at least one percent of its active sites converted to the silver form and preferably from about 30 to about 70 percent of its active sites converted to the silver form.

U.S. Pat. No. 5,801,279 to Miura et al discloses a method of operating a silver exchanged macroreticular strong acid ion exchange resin bed for removing iodides from a Monsanto type acetic acid stream. The operating method involves operating the bed while elevating the temperatures in stages and contacting the acetic acid and/or acetic anhydride containing the iodide compounds with the resins. Exemplified in the patent is the removal of hexyl iodide from acetic acid at temperatures of from about 25° C. to about 45° C.

So also, other ion exchange resins have been used to remove iodide impurities from acetic acid and/or acetic anhydride. There is disclosed in U.S. Pat. No. 5,220,058 to Fish et al the use of ion exchange resins having metal exchanged thiol functional groups for removing iodide impurities from acetic acid and/or acetic anhydride. Typically, the thiol functionality of the ion exchange resin has been exchanged with silver, palladium, or mercury.

There is further disclosed in European Publication No. 0 685 445 A1 a process for removing iodide compounds from acetic acid. The process involves contacting an iodide containing acetic acid stream with a polyvinylpyridine at elevated temperatures to remove the iodides. Typically, the acetic acid was fed to the resin bed according to the '445 publication at a temperature of about 100° C.

With ever increasing cost pressures and higher energy prices, there has been ever increasing motivation to simplify chemical manufacturing operations and particularly to reduce the number of manufacturing steps. In this regard, it is noted that in U.S. Pat. No. 5,416,237 to Aubigne et aL there is disclosed a single zone distillation process for making acetic acid. Such process modifications, while desirable in terms of energy costs, tend to place increasing demands on the purification train. In particular, fewer recycles and fewer purification steps tend to introduce (or fail to remove) a higher level of iodides into the product stream and particularly more iodides of a higher molecular weight. For example, octyl iodide, decyl iodide and dodeycl iodides may all be present in the product stream as well as hexadecyl iodide.

The prior art resin beds operated as described above do not efficiently and quantitatively remove higher organic iodides from organic media such as acetic acid or acetic acid streams as required by certain end uses, particularly the manufacture of vinyl acetate monomer. Accordingly, an object of the present invention is to provide for the efficient and nearly quantitative removal of higher organic iodides from an acetic acid and/or acetic anhydride product stream.

SUMMARY OF INVENTION

There is provided in a first aspect of the present invention, a method of removing organic iodides from non-aqueous organic media comprising contacting the organic media with a silver or mercury exchanged cationic ion exchange substrate at a temperature greater than about 50° C. Generally the organic media contains organic iodides with an aliphatic chain length of C10 or greater. In many embodiments the organic media contains organic iodides at least about 25 percent by weight of which have an aliphatic chain length of C10 or greater. In still other embodiments at least about 50 percent of the organic iodides include organic iodides having a chain length of C10 or greater. Such iodides may be selected from the group consisting of decyl iodide and dodecyl iodide. Preferably the treatment of the organic media is effective to remove at least about 90 percent by weight of the decyl iodides and dodecyl iodides from the organic media. Organic media in some embodiments contains total iodides in the range of from about 10 ppb to about 1000 ppb. More typically the organic media contains from about 250 ppb total iodide to about 750 ppb total iodide. Treatment of the organic media in accordance with the present invention preferably removes at least about 99 percent of the total iodides from the organic media There is provided in accordance with another aspect of the present invention a method of removing iodides from acetic acid or acetic anhydride including the steps of: (1) providing a stream of acetic acid or acetic anhydride with an organic iodide content wherein at least about 20 percent of said organic iodides comprise C10 or higher molecular weight organic iodides; (2) contacting said stream with a macroreticular, strong acid, ion exchange resin wherein at least about one percent of the active sites of the resin have been converted to the silver or mercury form. The bed is operated at a temperature (that is, the resin is maintained at a temperature) of at least about 50° C. and is operative to remove at least about 90 percent of the organic iodides in the stream of acetic acid or acetic anhydride. Most typically, the method is practiced on an acetic acid stream. Typical temperatures may include temperatures of at least about 60° C., at least about 70° C. or at least about 80° C. depending upon the flow rates and the nature of the iodides sought to be removed. The upper limit may be about 100° C. or up to 150° C. provided the resin selected is stable at these temperatures.

Most typically the resin is a sulfonic acid functionalized resin, wherein from about 25 to about 75 percent of the active sites have been converted to the silver form, whereas the product stream, prior to contacting the resin, has an iodide content of greater than about 100 ppb organic iodide. After contacting the resin, the stream, which initially had greater than 100 ppb organic iodide, typically has less than 20 ppb iodide and more desirably has less than about 10 ppb organic iodide.

In some embodiments the stream may, prior to contacting said resin, have an organic iodide content of greater than about 200 ppb. In such instances the ion exchange resin is operative to reduce the organic iodide content of the stream to less than about 20 ppb and desirably to less than about 10 ppb. Most preferably the ion exchange resin employed is a silver exchanged, strong acid styrene/divinyl benzene sulfonated resin wherein from about 1 to about 95 percent of the functional sites have been converted to the silver form.

Generally, the process of the present invention is effective to remove at least about 95 percent of the organic iodides in the product stream.

As used herein, unless otherwise indicated, ppb means parts per billion by weight of the mixture, ppm indicates parts per million by weight of the mixture, and percent, "%" indicates weight percent of the mixture or weight percent of the component as the context indicates.

BRIEF DESCRIPTION OF DRAWINGS

The invention is described in detail below in connection with the various FIGS. In the FIGS..

DETAILED DESCRIPTION

Figure 1:
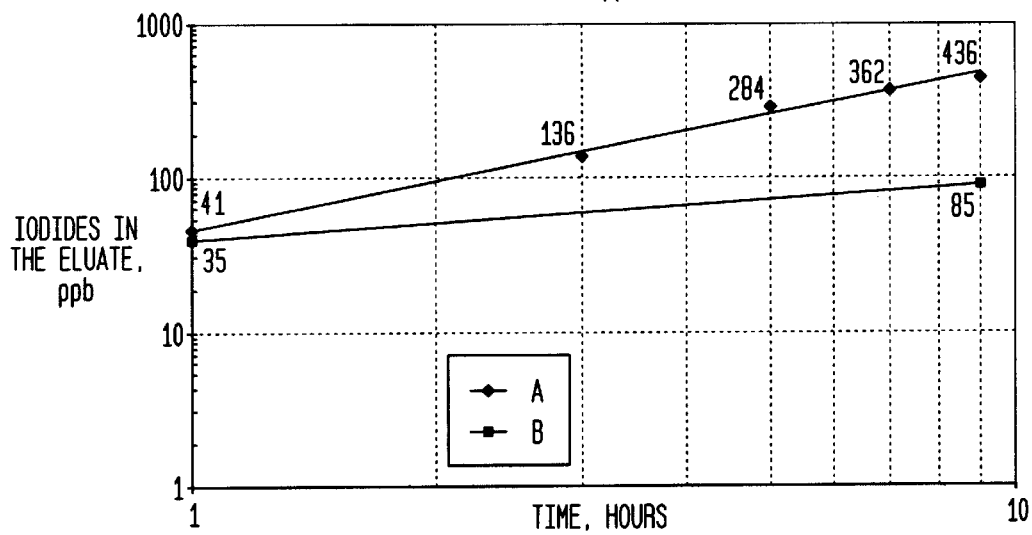
FIG. 1 is a plot of iodide concentration in treated acetic acid vs. time for commercial samples of material from the residue of a drying column wherein treatment is carried out at ambient conditions.

The method of the present invention is suitable for removing iodide compounds from non-aqueous organic media Such media may be organic acids, organic acid anhydrides, alcohols, ethers, esters, and the like. Media of particular importance include acetic acid and acetic anhydride by the term "non-aqueous" it is simply meant that water is not present to any significant extent, not typically present in an amount significantly past its solubility in the organic medium being processed. Generally, not present by more than 1%, and typically not present by more than 0.5% even in the case of organic media which are highly miscible with water.

The total amount of iodide present in the organic medium will vary depending upon the specific nature of the organic medium. Generally total iodide will not exceed 1000 parts per billion (ppb) when processed in accordance with the present invention, but will typically fall within the range from about 5 to about 500 ppb.

The invention is particularly useful for removing high molecular weight organic iodide compounds from acetic acid as may be encountered in a Monsanto type carbonylation process wherein it is desired to minimize the components utilized in the purification train as disclosed, for example, in U.S. Pat. No. 5,416,237 to Aubigne et al., the disclosure of which is incorporated herein by reference as if set forth in its entirety. Without a heavy ends treatment column or optional finishing distillation column, the removal of higher molecular weight iodides from the product stream is necessary in order to meet product specifications for iodide, especially for iodide-sensitive end uses such as the manufacture of vinyl acetate monomer as will be appreciated by one of skill in the art.

Ion exchange resins or other suitable substrates are typically prepared for use in connection with the present invention by exchanging anywhere from about 1 to about 99 percent of the active sites of the resin to the silver or mercury form by contacting the resin with a silver or mercury salt, as is taught for example in U.S. Pat. Nos.: 4,615,806; 5,139,981; 5,227,524 the disclosures of which are hereby incorporated by reference.

Suitably stable ion exchange resins utilized in connection with the present invention typically are of the "$RSO_3H$" type classified as "strong acid", that is, sulfonic acid, cation exchange resins of the macroreticular (macroporous) type. Particularly suitable ion exchange substrates include Amberlyst® 15 resin (Rohm and Haas), being particularly suitable for use at elevated temperatures. Other stable ion exchange substrates such as zeolites may be employed, provided that the material is stable in the organic medium at the conditions of interest, that is, will not chemically decompose or release silver or mercury into the organic medium in unacceptable amounts. Zeolite cationic ion exchange substrates are disclosed for example, in U.S. Pat. No. 5,962,735 to Kulprathipanja el al., the disclosure of which is incorporated herein by reference.

At temperatures greater than about 50° C., the silver or mercury exchanged cationic substrate may tend to release only small amounts of silver on the order of 500 ppb or less and thus the silver or mercury exchanged substrate is chemically stable under the conditions of interest. More preferably silver losses are less than about 100 ppb into the organic medium and still more preferably less than about 20 ppb into the organic medium. Silver losses may be slightly higher upon start up or if the process is conducted such that it may be exposed to light, since silver iodide is believed photoreactive and may form soluble complexes if contacted by light. In any event, if so desired, a bed of cationic material in the unexchanged form may be placed downstream of the silver or mercury exchange material of the present invention.

The process of the present invention may be carried out in any suitable configuration. A particularly preferred configuration is to utilize a bed of particulate material (termed herein a "guard bed") inasmuch as this configuration is particularly convenient. A typical flow rate, such as is used when acetic acid is to be purified, is from about 0.5 to about 20 bed volumes per hour (BV/hr). A bed volume of organic medium is simply a volume of the medium equal to the volume occupied by the resin bed. A flow rate of 1 BV/hr then means that a quantity of organic liquid equal to the volume occupied by the resin bed passes through the resin bed in a one hour time period. Preferred flow rates are usually from about 6 to about 10 BV/hr whereas a preferred flow rate is frequently about 6 BV/hr.

The invention is better understood by reference to the following examples.

EXAMPLES

The following examples used the procedures described below. Iodide removal was performed using silver exchanged Amberlyst® 15 resin. The resin (100 ml wet) was loaded into a 22 mm OD glass column and acetic acid containing iodides was eluted at a flow rate of 13.3 ml/min. Iodide levels in the eluate were measured every two (2) hours. Total iodides are measured in the eluate by any suitable technique. One suitable technique is by way of neutron activation analysis (NAA) as is well known in the art. The iodide levels for particular species were also measured. A preferred method in this latter respect is gas chromatography utilizing an electron capture detector.

Comparative Examples A and B

Samples of the residue from the drying column of a conventional Monsanto type acetic acid plant containing 540 ppb total iodide and 238 ppb total iodide were treated at room temperature using a silver exchanged bed of Amberlyst® 15 (CZ-B) resin and the total iodides in the eluate were measured as a function of time as shown in FIG. 1. As can be seen from FIG. 1, total iodide removal was typically less than about 90% and progressively decayed over a ten hour time period to much lower removal efficiencies.

The various iodide components in the feed were identified to include:

methyl iodide
ethyl iodide
2-iodo-2-methyl propane
propyl iodide
2-butyl iodide
butyl iodide
iodine
pentyl iodide.
hexyl iodide
octyl iodide
decyl iodide
dodecyl iodide
hexadecyl iodide The predominant high molecular weight organic iodide components identified were decyl iodide and dodecyl iodide.

Comparative Examples of C and D and Example 1

Figure 2:
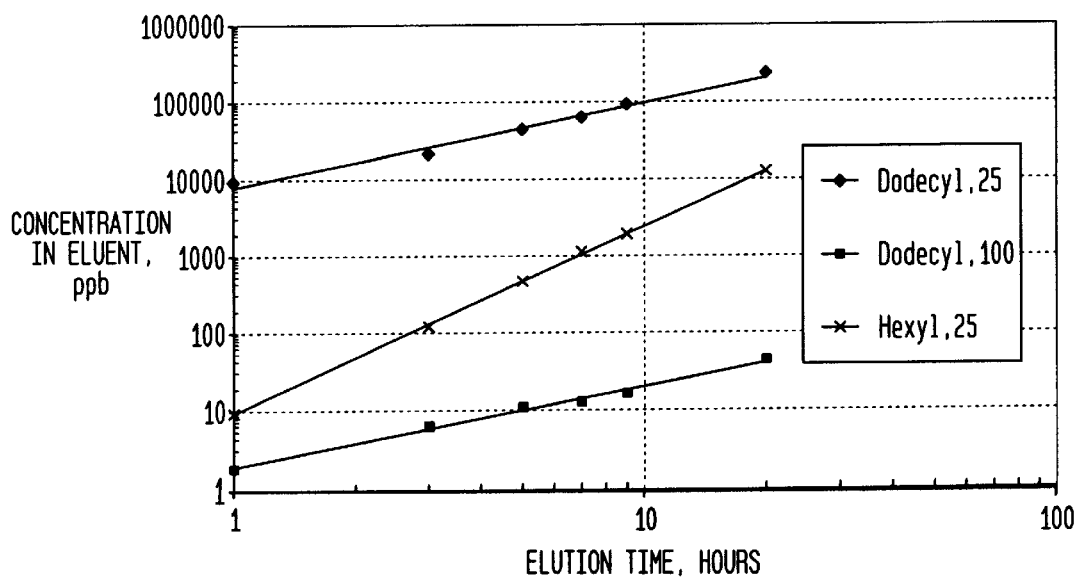
FIG. 2 is a plot of iodide in acetic acid eluent vs. time for dodecyl iodide and hexyl after treatment at various temperatures.

Following the procedure outlined above, the temperature dependence of the guard bed performance was measured for relatively high (ppm) levels of organic iodides in acetic acid. Results for dodecyl iodide and hexyl iodide at 25° C. and 100° C. are shown in FIG. 2. Results indicate that guard bed performance is greatly enhanced at 100° C. over 25° C., for dodecyl iodide. Performance improvements include both removal efficiency and useful life of the bed.

Comparative Examples E,F

Figure 3:
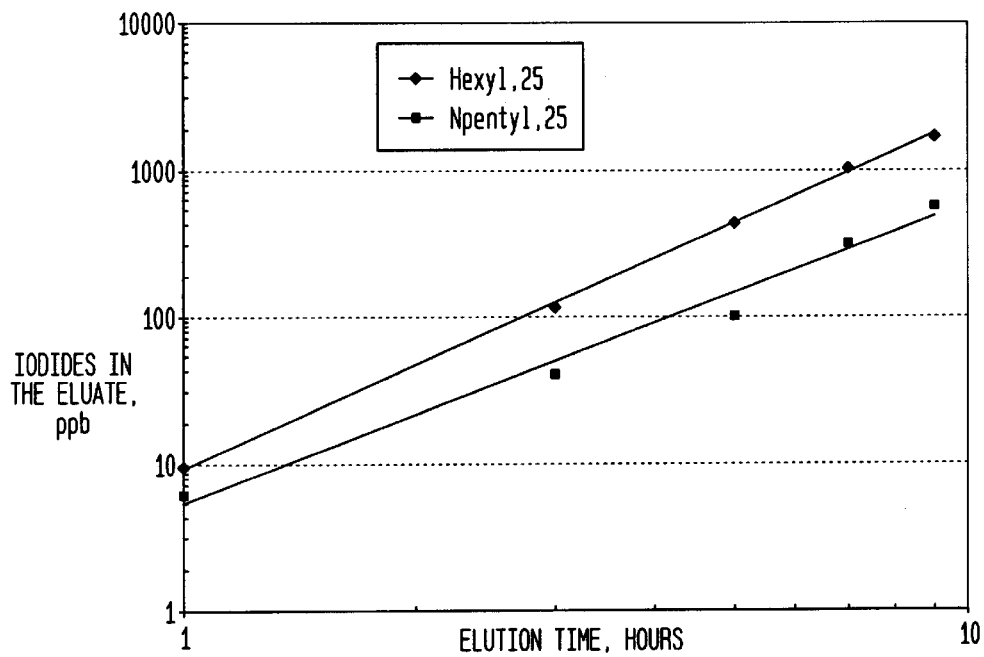
FIG. 3 is a plot of iodide vs. time in acetic acid eluent after treatment for hexyl iodide and neopentyl iodide.

Following the procedure outlined above, the effect of chain branching on guard bed performance was investigated by comparing removal of hexyl iodide with removal of neopentyl iodide. Results appear in FIG. 3.

Examples 2–4 and Comparative Examples G and H

Figure 4:
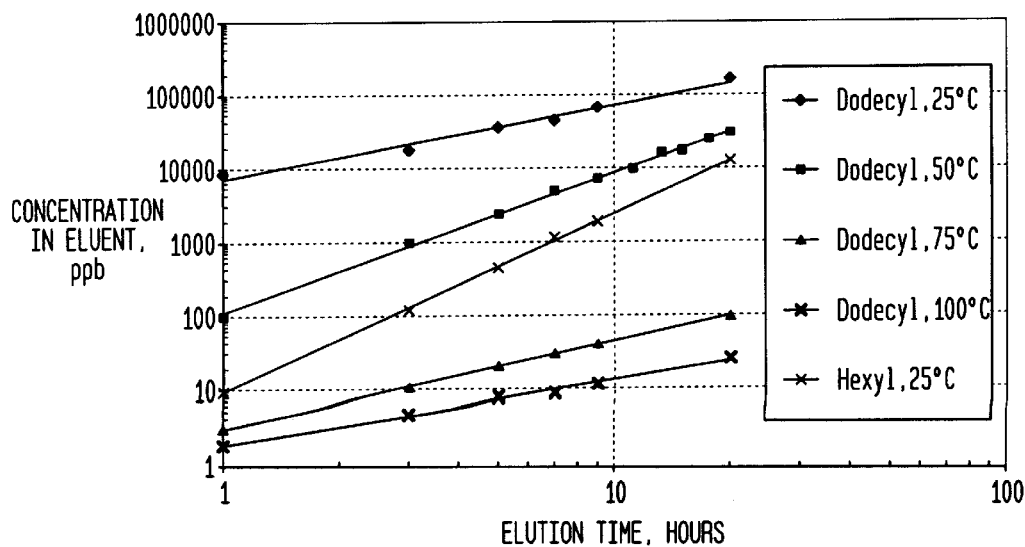
FIG. 4 is a plot of various elution isotherms at 25° C. to 100° C. for alkyl iodide removal from acetic acid.

Following the procedure outlined above, performance of a silver-exchanged Amberlyst® 15 guard bed was evaluated for removal of dodecyl iodide at 25° C., 50° C., 75° C., and 100° C. and for removal of hexyl iodide at 25° C. Results appear in FIG. 4. Here again, it can be seen removal efficiencies and useful capacities of the bed are greatly enhanced at temperatures above about 50° C.

Example 5 and Comparative Examples J and K

Figure 5:
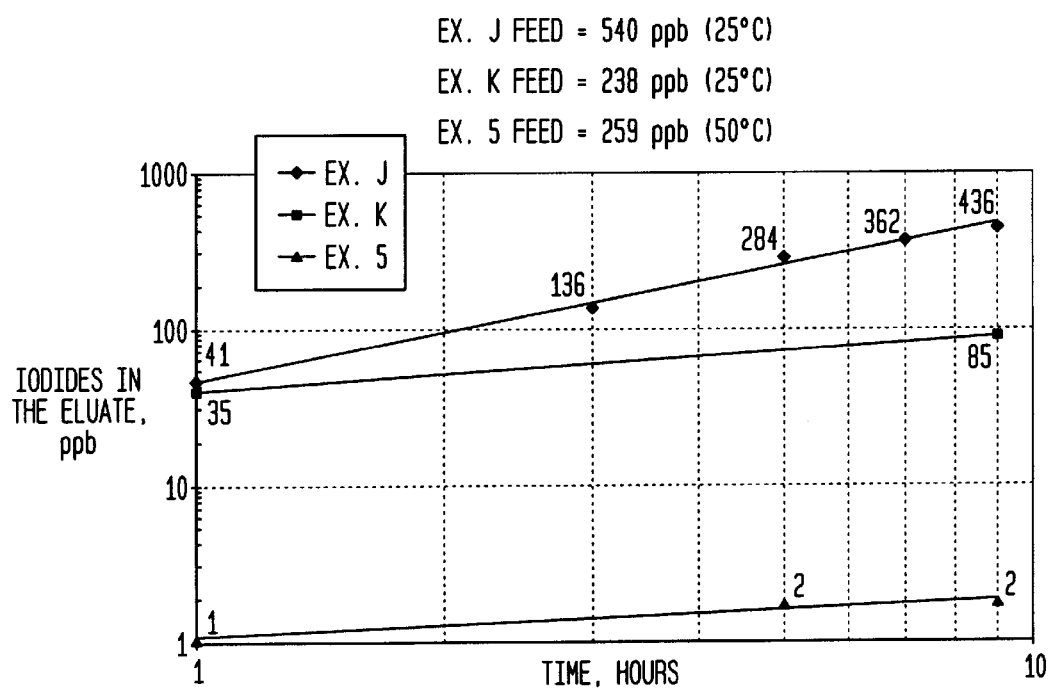
FIG. 5 is a plot of iodide concentration in acetic acid eluent vs. time for commercial samples of material treated at 25° C. and in accordance with the present invention.

Following the procedures outlined above, samples of acetic acid (drying column residue) from a Monsanto type of acetic acid plant were obtained containing respectively 540 ppb total iodide, 238 ppb total iodide and 259 ppb total iodide. The acid was treated, as before, using a silver exchanged Amberlyst® 15 guard bed at 25° C. and 50° C. Results appear in FIG. 5. As can be seen from FIG. 5, performance at 50° C. was far superior to removal efficiencies at 25° C. Indeed the guard bed removed greater than 99% (nearly quantitative removal) of the total iodide at 50° C.

While the invention has been described in detail and exemplified, various modifications will be readily apparent to those of skill in the art. For example, one may utilize an ion exchange resin suited for higher temperatures in connection with the present invention. Such modifications are within the spirit and scope of the present invention which is defined in the appended claims.

What is claimed is:

1. A method of removing organic iodides from non-aqueous organic media containing C10 and higher organic iodides comprising contacting said organic media with a silver or mercury exchanged cationic ion exchange substrate at a temperature greater than 50° C.

2. The method according to claim 1, wherein said organic media contains organic iodide with an aliphatic chain length of C10 or greater.

3. The method according to claim 2, wherein said organic media contains organic iodides, at least 25% by weight of which have an aliphatic chain length of C10 or greater.

4. The method according to claim 3, wherein at least about 50% of the organic iodide in said organic media comprise organic iodides having an aliphatic chain length of C10 or greater.

5. The method according to claim 1, wherein said organic iodides comprise iodides selected from the group consisting of decyl iodide and dodecyl iodide.

6. The method according to claim 5, wherein said treatment is effective to remove at least about 90% by weight of the decyl iodide and dodecyl iodide from the organic medium.

7. The method according to claim 1, wherein said organic medium has from about 10 to about 1000 ppb total iodides prior to treatment with said silver or mercury exchanged cationic ion exchange substrate.

8. The method according to claim 7, wherein said non-aqueous organic media contains from about 20 to about 750 ppb total iodides.

9. The method according to claim 8, wherein said treatment of contacting said organic media with said silver or mercury exchanged cationic ion exchange substrate at a temperature greater than about 50° C. is effective to remove at least about 99% by weight of the total iodide present in said organic media.

10. A method of removing iodides from acetic acid or acetic anhydride comprising:
   (a) providing a stream of acetic acid or acetic anhydride with an iodide content wherein at least about 20 percent by weight of the organic compounds in the product stream comprise C10 and higher organic iodides;
   (b) contacting said stream with a macroreticular, strong acid, ion exchange resin wherein at least about 1 percent of the active sites of said resin have been converted to the silver or mercury form, at a temperature of at least about 50° C.; and
   (c) wherein said silver or mercury exchanged ion exchange resin is effective to remove at least about 90 percent by weight of said organic iodides in said product stream of acetic acid or acetic anhydride.

11. The method according to claim 10, wherein said stream is an acetic acid stream.

12. The method according to claim 10, wherein said step of contacting said stream with said resin is at a temperature of at least about 60° C.

13. The method according to claim 10, wherein said step of contacting said stream with said resin is at a temperature of at least about 70° C.

14. The method according to claim 10, wherein said step of contacting said stream with said resin is at a temperature of at least about 80° C.

15. The method according to claim 10, wherein said ion exchange resin is a sulfonic acid functionalized resin.

16. The method according to claim 10, wherein said stream, prior to contacting said resin, has an iodide content of greater than about 100 ppb by weight organic iodide.

17. The method according to claim 16, wherein said stream, after contacting said resin, has an organic iodide content of less than 20 ppb.

18. The method according to claim 17, wherein said stream, after contacting said resin, has an iodide content of less than 10 ppb.

19. The method according to claim 10, wherein said stream, prior to contacting said resin, has an organic iodide content of greater than about 200 ppb by weight.

20. The method according to claim 19, wherein said stream, after contacting said resin, has an iodide content of less than 20 ppb by weight.

21. The method according to claim 20, wherein said stream, after contacting said resin, has an iodide content of less than 10 ppb by weight.

22. The method according to claim 10, wherein said ion exchange resin is a silver exchanged ion exchange resin.

23. The method according to claim 22, wherein from about 25 to about 75% of the active sites of said ion exchange resin have been converted to the silver or mercury form.

24. The method according to claim 10, wherein said ion exchange resin is a styrene/divinyl benzene ion exchange resin.

25. The method according to claim 10, wherein said ion exchange resin is effective to remove at least about 95% by weight of the organic iodides in said stream of acetic acid or acetic anhydride.

26. A method of removing organic iodides from acetic acid or acetic anhydride comprising contacting acetic acid or acetic anhydride containing dodecyl iodide with a silver or mercury exchanged cationic ion exchange substrate at a temperature of greater than about 50° C.

27. The method according to claim 26, wherein said step of contacting said acid or acetic anhydride with said silver or mercury exchanged cationic ion exchange substrate is carried out at a temperature of at least about 60° C.

28. The method according to claim 27, wherein said step of contacting said acid or acetic anhydride with said silver or mercury exchanged cationic ion exchange substrate is carried out at a temperature of at least about 70° C.

29. The method according to claim 28, wherein said step of contacting said acid or acetic anhydride with said silver or mercury exchanged cationic ion exchange substrate is carried out at a temperature of at least about 80° C.

* * * * *